US011497942B2

(12) United States Patent
Kröpke et al.

(10) Patent No.: US 11,497,942 B2
(45) Date of Patent: Nov. 15, 2022

(54) COSMETIC OR DERMATOLOGICAL PREPARATION COMPRISING A COMBINATION OF A DYE AND AN ANTI-INFLAMMATORY ACTIVE INGREDIENT

(75) Inventors: Rainer Kröpke, Schenefeld (DE); Ludger Kolbe, Dohren (DE); Anette Bürger, Hamburg (DE); Claudia Mundt, Bremen (DE)

(73) Assignee: BEIERSDORF AG, Hamburg (DE)

( * ) Notice: Subject to any disclaimer, the term of this patent is extended or adjusted under 35 U.S.C. 154(b) by 614 days.

(21) Appl. No.: 11/004,617

(22) Filed: Dec. 3, 2004

(65) Prior Publication Data
US 2005/0158259 A1 Jul. 21, 2005

(30) Foreign Application Priority Data

Dec. 4, 2003 (DE) ................ 103 57 046.2

(51) Int. Cl.
| | |
|---|---|
| *A61Q 19/00* | (2006.01) |
| *A61K 9/14* | (2006.01) |
| *A61K 8/34* | (2006.01) |
| *A61K 8/29* | (2006.01) |
| *A61K 8/42* | (2006.01) |
| *A61K 8/26* | (2006.01) |
| *A61K 8/92* | (2006.01) |
| *A61K 9/00* | (2006.01) |
| *A61K 8/19* | (2006.01) |

(52) U.S. Cl.
CPC .............. *A61Q 19/002* (2013.01); *A61K 8/19* (2013.01); *A61K 8/26* (2013.01); *A61K 8/29* (2013.01); *A61K 8/347* (2013.01); *A61K 8/42* (2013.01); *A61K 8/922* (2013.01); *A61K 9/0014* (2013.01); *A61Q 19/00* (2013.01); *A61Q 19/004* (2013.01); *A61K 2800/438* (2013.01)

(58) Field of Classification Search
USPC ..................................... 424/401, 1
See application file for complete search history.

(56) References Cited

U.S. PATENT DOCUMENTS

| | | | | |
|---|---|---|---|---|
| 3,873,687 A | * | 3/1975 | Demko ............................ | 424/64 |
| 5,478,555 A | * | 12/1995 | Bara et al. .................... | 424/78.03 |
| 5,804,203 A | * | 9/1998 | Hahn et al. ..................... | 424/401 |
| 6,074,652 A | | 6/2000 | Ishiwatari et al. | |
| 6,440,437 B1 | * | 8/2002 | Krzysik ............... | A61K 8/0208 |
| | | | | 424/400 |
| 6,485,756 B1 | | 11/2002 | Aust et al. | |
| 6,492,326 B1 | | 12/2002 | Robinson et al. | |
| 6,740,312 B2 | | 5/2004 | Chopin et al. | |
| 2001/0007677 A1 | * | 7/2001 | Nagatani et al. ............ | 424/401 |
| 2002/0025348 A1 | | 2/2002 | Basu et al. | |
| 2002/0115622 A1 | * | 8/2002 | Kumagai et al. ................ | 514/33 |
| 2003/0091666 A1 | | 5/2003 | Murad | |
| 2005/0037042 A1 | | 2/2005 | Dieck et al. | |
| 2005/0136139 A1 | | 6/2005 | Kruse et al. | |
| 2005/0158350 A1 | | 7/2005 | Max et al. | |
| 2005/0191266 A1 | | 9/2005 | Raschke et al. | |
| 2005/0201967 A1 | | 9/2005 | Albrecht et al. | |

FOREIGN PATENT DOCUMENTS

| | | |
|---|---|---|
| EP | 1216693 B2 | 6/2002 |
| GB | 1 529 599 | 10/1978 |
| JP | 7-2656 | 1/1995 |
| JP | 9-227353 | 9/1997 |
| JP | 10-77221 | 3/1998 |
| JP | 2002363054 A * | 12/2002 |
| JP | 2003-238379 | 8/2003 |
| WO | 9603962 A1 | 2/1996 |
| WO | 0051551 A2 | 9/2000 |
| WO | WO 01/45725 A2 | 6/2001 |
| WO | 0152795 A2 | 7/2001 |
| WO | WO 01/85183 A2 | 11/2001 |
| WO | WO 02/00190 A1 | 1/2002 |
| WO | WO 02/15873 * | 2/2002 ............... A61K 7/48 |
| WO | WO 02/15873 A2 | 2/2002 |
| WO | 03/057233 | 7/2003 |
| WO | 03/101414 | 12/2003 |
| WO | WO 03/105787 A2 | 12/2003 |

OTHER PUBLICATIONS http://www.walgreens.com/store/product.jsp?CATID=100738&navAction=jump&navCount=1&id=prod1401814.*
Wenninger, J. A. & McEwen, Jr., G. N. (1997). International Cosmetic Ingredient Dictionary and Handbook (pp. 301-307). Washington, DC: The Cosmetic, Toiletry, and Fragrance Association.*
Cohen, A. F., et al. J. Am. Board. Fam. Pract. 2002, 15, 214-7.*
Millikan, L. Skinmed: Dermatology for the Clinician 2003, 2, 43-47; available at: http://www.lejacq.com/Search_ArticleDetail.cfm?PID=Skinmed_2;1:43&CFID=1793192&CFTOKEN=81620654.*
Shibata, S., et al. Planta Medica 1991, 57, 221-224.*
Kolbe, L., et al. Arch. Dermatol. Res. 2006, 298, 23-30.*
Eucerin: Dermatologist-Preferred Skin Care, available at: http://www.eucerinus.com/products/face_err_dailylotion.html.*
Alfonso R. Gennaro, Remington's: the Science and Practice of Pharmacy, 1995, nineteenth Edition, vol. 1, p. 806.*
Tsukiyama et al. "Antibacterial Activity of Licochalcone A against Spore-Forming Bacteria" Antimicrobial Agents and Chemotherapy, May 2002, p. 1226-1230.*
Translation of Oto et al. JP 2002-363054 A (Jan. 2011).*
Bikowski, J., "The use of therapeutic mosturizers in various dermatologic disorders" Cutis, Dec. 2001, vol. 68, issue. 5, p. 3-11.*
European Search Report for German Application No. 04105637 dated Mar. 30, 2005.

(Continued)

Primary Examiner — Shengjun Wang
(74) Attorney, Agent, or Firm — Abel Schillinger, LLP

(57) ABSTRACT

The present invention is a cosmetic or dermatological preparation comprising 0.01% by weight to 5% by weight of at least one red light-filtering dye and 0.0001% by weight to 10% by weight of at least one anti-inflammatory active ingredient. The preparation can be used for the prophylaxis and treatment of sun-irritated skin and to aid the body's own repair mechanisms.

38 Claims, No Drawings

(56) References Cited

OTHER PUBLICATIONS

U.S. Appl. No. 10/571,530, filed Mar. 10, 2006 and entitled "Use of licochalcone A or of an extract containing licochalcone A from radix glycyrrhizae inflatae against aging skin".
U.S. Appl. No. 10/581,271, filed Jun. 1, 2006 and entitled "Combination of 2,3-dibenzylbutyrolactone and licochalcone-A".
U.S. Appl. No. 11/514,214, filed Sep. 1, 2006 and entitled "Active substance combination of licochalcone A and phenoxyethanol".
U.S. Appl. No. 11/586,538, filed Oct. 26, 2006 and entitled "Use of licochalcone A against rosacea".
Jones, L.M. "Drug Dosage Forms" in Jones, L.M., et al., Veterenary Pharmacology and Therapeutics, 3$^{rd}$ ed. Iowa State University Press 1995, pp. 14-17.
Blodinger, J. "Formulation of Drug Dosage Forms for Animals" in: Biodinger J., Formulation of Veterinary Dosage Forms, Marcel Dekker Inc., New York 1983, pp. 135-173, in particular p. 147.
Tsukiyama, R-I, et al., Antimicrob. Agents Chemother. 2002, 46(5): pp. 1226-1230.
Djaković et al., "Rosacea as a multisystemic disease", Srp Arh Celok Lek. vol. 131, No. 11-12 (2003), pp. 478-479, PubMed abstract only.
http://web.archive.org/web/*/http://www.kaviskin.com/skin_care.php.
http:// web.archive.org/web/*/http://www.eltean.com/skin.htm.
http://web.archive.org/web/*/http://bodd.cf.ac.uk/BotDermFolder/BotDermL/LEGU.html, Dec. 13, 2005.
http://www.ibiblio.org/pfaf/cgi-bin/arr_html?Glycyrrhiza+glabra, Dec. 13, 2005.
http://web.archive.org/web/*/http://www.herbasin.com/database/gancao.htm, Dec. 8, 2005.
Sovak M. et al., J. Natl. Cancer Inst. 2002; 94(17), pp. 1275-1281, especially p. 1280.
English Language Abstract of JP 10-77221.
English Language Abstract of JP 2003-238379.
English Language Abstract of JP 7-2656.
English Language Abstract of JP 9-227353.

\* cited by examiner

COSMETIC OR DERMATOLOGICAL PREPARATION COMPRISING A COMBINATION OF A DYE AND AN ANTI-INFLAMMATORY ACTIVE INGREDIENT

FIELD OF THE INVENTION

The present invention relates to cosmetic or dermatological preparations that include a combination of a dye and an anti-inflammatory active ingredient, and particularly to preparations for the prophylaxis and treatment of sun-irritated skin that aid the body's own repair mechanisms. In addition, the invention relates to the use of such preparations comprising such combinations.

BACKGROUND OF THE INVENTION

The skin, in particular the epidermis, is a barrier organ of the human organism and is subjected to external effects to a particular degree. According to current scientific understanding, the skin represents an immunological organ which, being an immunocompetent peripheral compartment, plays its own role in inductive, effective and regulative immuno-processes of the entire organism.

The epidermis is richly equipped with nerves and nerve ending apparatuses, such as Vater-Pacini lamellar bodies, Merkel cell neurite complexes and free nerve endings for pain, cold, heat sensation and itching.

In people with sensitive, tender or injured skin, a neurosensory phenomenon referred to as "stinging" may be observed. This "sensitive skin" differs in principle from "dry skin" with thickened and hardened horny layers.

Typical reactions of "stinging" with sensitive skin are reddening, tightening and burning of the skin, and also itching.

"Stinging" phenomena can be regarded as disorders to be treated cosmetically. By contrast, severe itching, in particular severe itching which arises with atopy, and itching in cases of skin disorders can also be referred to as a more serious dermatological disorder or neurosensory phenomenon.

Typical undesired neurosensory phenomena associated with the terms "stinging" or "sensitive skin" are skin reddening, prickling, tingling, tightening and burning of the skin and itching. They can be caused by stimulating environmental conditions—e.g. massage, effect of (washing-active) surfactants, weather effects such as sun, cold, dryness, but also moist heat, thermal radiation and UV radiation, e.g. from the sun.

In "Journal of the Society of Cosmetic Chemists" 28, pp. 197-209 (May 1977), P. J. Frosch and A. M. Kligman describe a method for estimating the "stinging potential" of topically applied substances. The positive substances used here are, for example, lactic acid and pyruvic acid. However, when measuring by this method, amino acids, in particular glycine, were also ascertained as being neurosensorily active (such substances are called "stingers").

According to findings hitherto, such a sensitivity towards very specific substances arises differently depending on the individual. This means that someone who suffers "stinging effects" upon contact with a substance will more likely suffer again upon any further contact. Contact with other "stingers" may, however, be just as likely without any reaction.

When using some deodorizing or antiperspirant preparations as well, many more or less sensitive people have to suffer from erythematous skin symptoms.

In addition, erythematous skin symptoms also arise as accompanying symptoms with certain skin disorders or irregularities. For example, the typical skin eruption in the appearance of acne is regularly reddened to a greater or lesser degree.

Shaving also causes erythema, burning, itching and feelings of tightness in people sensitive thereto and are triggered by the surface injury and the mechanical strain on the uppermost layers of the skin both with wet-shaving and also with dry-shaving. These complaints often arise during the daily shaving of beard hair, but irritations may also arise after the shaving of armpit hair, pubic hair and leg hair.

Besides the positive effects of sunlight, such as general wellbeing, the formation of vitamin D3 and the treatment of acne, there are also negative effects which have to be counteracted.

For the human organism, the conditions of sunbathing represent unusual, at times extreme, exposure, from which the skin in particular is affected. Provided the radiation exposure does not exceed a certain level, our skin is ready for it. Slight damage, as arises with nontraceable suberythema is immediately repaired. If, however, the skin is exposed for too long to the sun or to a source of artificial rays, after a latency period of from 2 to 3 hours, a reddening of the skin, starkly demarcated from the unradiated skin, arises-Erythema solare. Sunburn which has arisen in this way is differentiated as follows:

1st degree: Erythema (reddening, feeling of warmth, burning, feeling of skin tightness) subsides again after 2 to 3 days and disappears with a simultaneous increase in pigmentation, 2nd degree: Blister formation
blisters form on the skin with burning and itching, and sections of the epidermis are shed, 3rd degree: Cell damage
deep cell damage occurs, the body reacts with fever, large sections of the epidermis are shed.

The 2nd and 3rd degrees are also referred to as Dermatitis solare.

The formation of erythema is dependent on the wavelength. The erythema region of UV-B is between 280 nm and 320 nm.

Sunbathing is regarded by most people as being pleasant, and the disadvantageous consequences are initially not taken into consideration. However, in recent years knowledge about the negative effects of excessive solar irradiation has emerged, for which reason more and stronger protecting sunscreens are applied.

Sun-hungry holidaymakers expose themselves to the sun to a great degree even at the start of the holiday. As a result, the risk of irritated, reddish skin or even slight sunburn is very great.

Sunburn and/or photoerythema are the acute manifestations of the effect of light. Besides the known harmful effects of the UV rays, in the after-reaction of the skin, the consequences are reduced sebum production and a drying out of the skin. The skin is treated using the so-called aftersun preparations, the use of which is in principle recommended after every exposure to the sun. These are generally emulsions or aqueous hydrogels which, besides customary moisturizing substances, can also comprise special active ingredients, such as, for example, inflammation-alleviating and cooling substances,
local anaesthetic substances and/or
disinfecting substances in order to prevent possible skin infections.

Use is made, for example, of inflammation-alleviating or -inhibiting active ingredients obtained from plants, such as azulene and bisabolol (camomile), glycyrrhizin (liquorice root), hamamelin (*Hamamelis*) or entire extracts, e.g. from aloe vera or camomile. These display certain successes in milder forms and locally limited erythema reactions. The same is true for creams with a high content of essential oils or panthenol.

Aftersun preparations are intended to cool the skin after sunbathing and to improve its moisturizing ability where the imparting of the cooling effect plays a central role. This cooling effect is achieved, for example, by large amounts of ethanol, which spontaneously evaporates when the formulation is distributed on the skin. Hydrogels, O/W emulsions (lotions) or aqueous lotions also have a marked cooling effect as a result of the cold due to evaporation of the aqueous phase, which leads to local vascular constriction and to an alleviation of inflammation.

Besides this unsightly reddish appearance of the skin caused by solar irradiation, many people suffer from couperosis (vascular dilations on the face), rosacea or other similar clinical pictures which involve an unnaturally reddened skin.

Rosacea is an hereditary noninfective skin disease which generally does not appear before the 30th year of life; those affected are often in their 5th decade of life. The result then is dilation of the blood vessels which causes the skin to "bloom" red. Inflammations may also sometimes occur around the sebaceous glands. These inflammatory processes cause pustules, but have nothing to do with acne.

The skin disease rosacea when translated means "rose blossoms". This alludes to the reddening in the face which is typical of rosacea. Besides this reddening, which arises due to dilated blood vessels, inflammations may also lead to changes to the nose.

Although to date the cause of rosacea has not been explained unequivocally, the cause is, however, obviously the so-called rosacea diathesis. This means the tendency to react to certain stimuli with marked facial reddening which subsides again after a time. This reddening state is also termed flush.

The reddening of the face as a reaction to external factors (change in temperature, spicy foods) can occur at any time and then subsides again normally. In people with a rosacea tendency, this increased circulation can lead to permanently dilated vessels (so-called telangiectasies), which are visible as thread-fine, red lines on the skin. These dilated vessels occur in particular around the sebaceous glands of the face and are the first sign of rosacea.

WO 0200190 describes cosmetic or pharmaceutical preparations which comprise one or more ingredients which emit green phosphorescent light. As is known, green light has an antioxidative effect (comorosan effect).

Moreover, from decorative cosmetics are known preparations which, applied to the skin, cover these areas of skin with colour.

SUMMARY OF THE INVENTION

It was an object of the present invention to overcome the disadvantages of the prior art and to provide preparations which give a natural appearance back to damaged skin. In particular, the object of the present invention was to provide preparations which can be applied to skin reddened by solar irradiation or disease-induced circumstances, such as rosacea, and lead to prophylaxis and treatment of sun-irritated skin and to the support of the body's own repair mechanisms.

The objects listed are achieved by preparations according to the main claim. The subject-matter of the dependent claims are advantageous embodiments of the preparations according to the invention. Furthermore, the invention covers the use of such preparations.

It was surprising, and herein lies the attainment of these objects, that cosmetic or dermatological preparations with a content of 0.01% by weight—5% by weight of red light-filtering dyes and 0.0001% by weight—10% by weight of anti-inflammatory active ingredients, preferably *Hamamelis, Glycyrrhiza inflata*, panthenol and/or camomile extract, overcome the disadvantages of the prior art. The percentages given are based on the total mass of the preparations.

The formulations according to the invention are extremely satisfactory preparations in every respect and are characterized by an excellent effect. The use of the active ingredients used according to the invention or of cosmetic or topical dermatological preparations with an effective content of active ingredients used according to the invention enables effective treatment, but also prophylaxis of inflammatory skin conditions, rosacea and, in particular, sun-irritated skin.

The preparations according to the invention allow on the one hand a visual concealment of rosacea and reddened skin, caused in particular by solar irradiation, and on the other hand long-lasting care of the skin.

A surprisingly synergistic effect arises due to the combination of the constituents according to the invention: an immediate effect due to the red light-filtering dyes (green pigments) and a long-term effect due to the anti-inflammatory active ingredients.

It was unforeseeable by the person skilled in the art that the preparations according to the invention would better care for photodamaged skin, better reduce the after-reactions of the skin to the effect of UV radiation, better calm skin irritated by sunbathing, cause slight sunburn to subside more quickly, allow reddened areas of skin to appear normal, restore a natural appearance, be easier to formulate, and be characterized by better care action, than the preparations of the prior art.

DETAILED DESCRIPTION OF THE PREFERRED EMBODIMENTS

The invention is of course not limited to preparations which are applied after sunbathing, but naturally includes all cosmetic and dermatological applications in which an inflammation-alleviating effect could be desirable or advantageous. Mention may be made here in particular also of shaving burn, as often arises after shaving.

The invention therefore further provides the use of cosmetic or dermatological formulations for the care of photodamaged and shaving-stressed skin and/or for the alleviation or the after-reactions of the skin to the effect of UV radiation and/or shaving, and for the treatment and care of reddened skin caused by disease, such as, for example, rosacea.

Preferred anti-inflammatory active ingredients are *Hamamelis, Glycyrrhiza inflata*, panthenol and camomile extract, and combinations thereof.

The plant species *Glycyrrhiza inflata* belongs, like the liquorice which is official in Europe *Glycyrrhiza glabra*, to the genus *Glycyrrhiza*, which belongs to the *Fabaceae* plant family (pea plants). The drug Radix *Glycyrrhizae inflatae*, i.e. the root of the plant, is used, for example, in Far Eastern medicine. The use of the drug as anti-inflammatory is likewise known.

A constituent of the aqueous extract of Radix *Glycyrrhizae inflatae* is licochalcone A, which is characterized by the following structural formula:

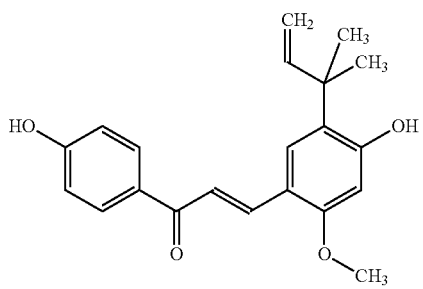 [SMILES: C=CC(C)(C)c1cc(/C=C/C(=O)c2ccc(O)cc2)c(OC)cc1O]

It is assumed that this substance, possibly in synergy with the other constituents of the extract, has part of the effect according to the invention.

The anti-inflammatory effect of licochalcone A is known per se. To achieve this effect in topical formulations, however, the solubility of licochalcone A in the vehicle and an adequate dermal bioavailability are important prerequisites. However, licochalcone A is a sparingly soluble substance which can crystallize out during storage and processing. This crystallization tendency represents a considerable problem since active ingredient crystals can lead to cosmetic inelegance, formula instabilities and/or loss of activity. According to the invention, it has therefore been achieved by the preparations according to the invention to increase the solubility of licochalcone A and thus its bioavailability. Accordingly, cosmetic or dermatological preparations with a content of licochalcone A in combination with red light-filtering dyes are also in particular in accordance with the invention.

Surprisingly the synergism is evident particularly advantageously if the cosmetic or dermatological preparations comprise 0.01% by weight to 10% by weight, in particular 0.05 to 5% by weight, very particularly 0.1 to 2% by weight, of anti-inflammatory active ingredient, in particular an aqueous extract from Radix *Glycyrrhizae inflatae*.

It is very particularly advantageous to start from an aqueous extract which is known under the name Aqua Licorice Extract P-U from Maruzen, which is an aqueous mixture (about 10% by weight water) of Radix *Glycyrrhizae inflatae* (about 5% by weight, content of licochalcones A in the extract about 22%), PPG-6 decyltetradeceth-30 (about 25% by weight) and butylene glycol (about 60% by weight). The extract can then advantageously be added in an amount of from 0.01 to 10% by weight.

It is also advantageous to use licochalcones A in other vehicle systems in a concentration of from 0.0001 to 5% by weight, in particular 0.001 to 1% by weight, very particularly 0.005-0.25% by weight. The active ingredient fraction in licochalcones is based on the total mass of the preparation.

Hamamelis is a further known anti-inflammatory substance. Hamamelis, known in its North American homeland as witch hazel, resembles our hazelnut bush and is therefore also sometimes called witch hazel. The *Hamamelis* leaves contain essential oils, tannins (gallotannins) and flavonoids which make the plant a medicinal plant. Hamamelis has an anti-inflammatory, antiseptic, contracting, decongestant, locally hemostatic, hypotensive, angioprotective effect. Hamamelis is used in many cosmetic care preparations for skin care, in face washes, shaving lotions and hair tonics, for wounds which do not heal well, skin inflammations, skin reddening, aching muscles, lumbago, varicose veins, haemorrhoids, vein disorders such as varices, rheumatic complaints and hair problems.

Panthenol, free international abbreviation for (±)-2,4-dihydroxy-N-(3-hydroxypropyl)-3,3-dimethylbutyramide (dexpanthenol, CTFA name: Panthenol)

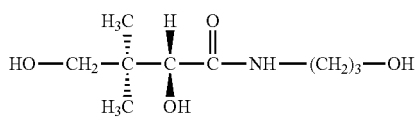

$C_9H_{19}NO_4$, $M_R$ 205.25. Only the D form is used as vitamin, which is converted to pantothenic acid in the organism. The pantothenic acid is thought to encourage hair growth, for which reason it is used for the preparation of hair tonics. In addition, panthenol has a soothing effect in cases of sunburn and stimulates pigmentation. Panthenol is often a constituent of moisturizing creams and exhibits a moisturizing effect. Panthenol is used primarily for the treatment of inflammation of the gastrointestinal canal, the eye and the skin, also for wound healing disorders and in hair tonics and also cosmetics.

Red light-filtering dyes, in particular green pigments, can be chosen from the corresponding positive list of the Cosmetics Directive or the EC list of cosmetic colorants. In most cases, they are identical to the dyes approved for foods.

Advantageous green pigments can be chosen from the following group alone or in combination: Colorona Brilliant Green, Colorona Egyptian Emerald, Timiron Splendid Green, Vert Oxyde Crome Anhydre N, Vert Oxydede Crome Hydrate W886 and/or Outremer Supercosmetique W 6803. These said pigments are inter alia also listed under the corresponding CI numbers. Preference is therefore given in particular to the green pigments with the CI numbers CI 77288, CI 77289, CI 77007, CI 77891, CI 77491, CI 77499, CI 77891, CI 77499, CI 77288 and CI 77492.

It is decisive for the dye that, when it is applied to a reddish or red background, it conveys a skin-coloured overall appearance. According to the invention, 0.01% by weight to 5% by weight, preferably 0.08 to 0.25% by weight, in particular 0.1 to 0.2% by weight, based on the total mass of the preparation, of red light-filtering dyes are therefore used.

Red light-filtering means here that the red light part of visible light is absorbed and the complementary colour green becomes visible.

By applying the preparation according to the invention containing red light-filtering dyes, such as, for example, the stated green pigments, to the skin which appears reddish in colour, for example as a result of solar irradiation or due to rosacea, the appearance of the skin will appear natural to the observer. In order to produce this effect, the choice and amount of red light-filtering dyes is significant. Moreover, an addition of white pigment is also advantageous, in particular all concealing, white pigments, in particular all titanium dioxides, bismuth oxides, barium sulphate. The white pigments readily cover the reddened skin and give a certain coverage. Without white pigments, a larger fraction of the other colour pigments is thus required.

The addition of blue pigments in the ratio 1:1 to 1:100, based on the green pigment used, is likewise recommended. The blue pigment increases the colour-changing effect, meaning that the reddish skin colour is better converted to a natural brown, i.e. a natural skin colour. According to the invention, this special colour effect is possible with or without white and/or blue pigments by using the red light-filtering dyes in an amount ranging from 0.01 to 5% by weight.

It is preferred for the purposes of the present invention if the cosmetic or dermatological preparations according to the invention comprise one or more alcohols, in particular if the formulations are to be in the form of an aftersun preparation and characterized by a particular cooling effect.

The cosmetic or dermatological formulations for the purposes of the present invention can preferably additionally comprise one or more water phases besides one or more oil phases and, for example, be in the form of W/O, O/W, W/O/W or O/W/O emulsions. Such emulsions may preferably also be a microemulsion, a Pickering emulsion or a sprayable emulsion.

Preferably, the formulations according to the invention also comprise further anti-inflammatory substances, such as, for example, allantoin, α-bisabolol, pantothenic acid, Royal jelly, azulene or Aloe-vera extract, and unsaponifiable fractions of avocado oil or soya oil and further substances which calm irritated skin. Further advantageous active ingredients are tannins, which have an astringent, anti-inflammatory and/or antisecretory effect.

Moreover, the formulations according to the invention can also advantageously comprise dihydroxyacetone or nut extracts and further substances which are thought to achieve tanning.

The cosmetic and/or dermatological formulations according to the invention can have the customary composition and be used, in particular, for the treatment and the care of the skin and/or the hair after sunbathing and as make-up product in decorative cosmetics. Accordingly, the formulations according to the invention may be used, depending on their formulation, for example as skin protection cream, cleansing milk, sunscreen lotion, nutrient cream, day or night cream etc. It is in some cases possible and advantageous to use the formulations according to the invention as a base for pharmaceutical formulations. Preference is given in particular to those cosmetic and dermatological formulations which are in the form of an aftersun skin care product or an aftershave product.

For use, the cosmetic and dermatological formulations according to the invention are applied to the skin and/or the hair in an adequate amount in the manner customary for cosmetics, i.e. for example directly—following removal from a bottle, tube, pot or other container—or using an (impregnated) wipe.

Impregnated wipes are used widely as objects of daily need in a very wide variety of fields. They allow, inter alia, efficient and skin-friendly cleaning and care, particularly also in the absence of (flowing) water. Here, the actual object of use consists of two components:
a) a dry wipe which is made of material such as paper and/or a very wide variety of mixtures of natural or synthetic fibres and
b) a low-viscosity impregnation solution.

The present invention thus also provides cosmetic and dermatological wipes which are moistened with cosmetic or dermatological impregnation solutions which have a content of active ingredient combination according to the invention.

"Dry" wipes (according to a)) preferred according to the invention consists of nonwoven, in particular water-jet-consolidated and/or water-jet-embossed nonwoven.

Such nonwovens can have macroimpressions in any desired pattern. The choice to be made is governed firstly by the impregnation to be applied and secondly by the field of use in which the later wipe is to be used.

It has proven advantageous for the wipe if it has a weight of from 35 to 120 g/m$^2$, preferably from 40 to 60 g/m$^2$ (measured at 20° C.±2° C. and at an atmospheric humidity of 65%+5% for 24 hours).

The thickness of the nonwoven is preferably 0.4 mm to 2 mm, in particular 0.6 mm to 0.9 mm.

The starting materials used for the nonwoven fabric of the wipe may generally be all organic and inorganic natural and synthetic fibre materials. Examples which may be mentioned are viscose, cotton, cellulose, jute, hemp, sisal, silk, wool, polypropylene, polyester, polyethylene terephthalate (PET), aramid, nylon, polyvinyl derivatives, polyurethanes, polylactide, polyhydroxyalkanoate, cellulose ester and/or polyethylene and also mineral fibres, such as glass fibres or carbon fibres. However, the present invention is not limited to the materials stated, but it is possible to use a large number of other fibres to form the nonwoven. In particular, it is advantageous for the purposes of the present invention if the fibres used are not soluble in water.

In a particularly advantageous embodiment of the nonwoven, the fibres consist of a mixture of 70% viscose and 30% PET.

Fibres of high-strength polymers such as polyamide, polyester and/or highly drawn polyethylene are also particularly advantageous.

Moreover, the fibres can also be coloured in order to be able to emphasize and/or enhance the visual attractiveness of the nonwoven. The fibres can additionally comprise UV stabilizers and/or preservatives.

The fibres used to form the wipe preferably have a water-absorption rate of more than 60 mm/[10 min] (measured using the EDANA test 10.1-72), in particular more than 80 mm/[10 min].

Furthermore, the fibres used to form the wipe preferably have a water-absorption capacity of more than 5 g/g (measured using the EDANA test 10.1-72), in particular more than 8 g/g.

It is advantageous for the purposes of the present invention if the weight ratio of the unimpregnated wipe to the impregnation solution is chosen from the range from 2:1 to 1:6.

The cosmetic and dermatological formulations or preparations according to the invention specified within the scope of the description of the present invention represent advantageous impregnation solutions for cosmetic and dermatological wipes for the purposes of the present invention.

It is advantageous if the impregnation solutions according to the invention are of low viscosity, in particular sprayable, and have, for example, a viscosity of less than 2000 mPa·s, in particular less than 1500 mPa·s (measuring instrument: Haake Viskotester VT-02 at 25° C.).

Preferred embodiment of the preparation according to the invention is therefore an emulsion, an aerosol, a concealer (cover stick) or a gel.

A preparation according to the invention as concealer (cover stick) is particularly suitable and thus preferred since even very small areas of skin can be treated in a targeted manner. In known guide formulations for suitable cover sticks with which the person skilled in the art is familiar, according to the invention the synergistic combination of dye and active ingredient is included, thus giving preparations according to the invention.

The cosmetic and dermatological formulations according to the invention can comprise cosmetic auxiliaries as are customarily used in such preparations, e.g. preservatives, bactericides, perfumes, substances for preventing foaming, dyes, pigments which have a colouring effect, thickeners, moisturizing and/or humectant substances, fats, oils, waxes or other customary constituents of a cosmetic or dermatological formulation, such as alcohols, polyols, polymers, foam stabilizers, electrolytes, organic solvents and/or silicone derivatives, and moisturizers.

Moisturizers is the term used for substances or mixtures of substances which, following application or distribution on the surface of the skin, impart to cosmetic or dermatological preparations the property of reducing the moisture loss by the horny layer (also called transepidermal water loss (TEWL)) and/or positively influencing hydration of the horny layer.

Advantageous moisturizers for the purposes of the present invention are, for example, glycerol, lactic acid, pyrrolidonecarboxylic acid and urea. It is also particularly advantageous to use polymeric moisturizers from the group of water-soluble and/or water-swellable and/or water-gellable polysaccharides. Particularly advantageous are, for example, hyaluronic acid and/or a fucose-rich polysaccharide which is listed in the Chemical Abstracts under the registry number 178463-23-5 and is available, for example, under the name Fucogel®1000 from SOLABIA S. A. Glycerol can be used as moisturizer for the purposes of the present application in the range from 0.05-30% by weight, particularly preferably 1-10%.

The amounts of cosmetic or dermatological auxiliaries and carrier substances and perfume to be used in each case can be determined easily by the person skilled in the art by simple experimentation, depending on the nature of the particular product.

An additional content of antioxidants is generally preferred. According to the invention, favourable antioxidants which can be used are all antioxidants customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulphoximine compounds (e.g. buthionine sulphoximines, homocysteine sulphoximine, buthionine sulphones, penta-, hexa-, heptathionine sulphoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, melanins, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, alanine diacetic acid, flavonoids, polyphenols, catechins, vitamin C and derivatives (e.g. ascorbyl palmitate, Mg ascorbyl phosphate, ascorbyl acetate), tocopherols and derivatives (e.g. vitamin E acetate), and coniferyl benzoate of benzoin resin, rutinic acid and derivatives thereof, ferulic acid and derivatives thereof, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenemethionine), stilbenes and derivatives thereof (e.g. stilbene oxide, trans-stilbene oxide) and the derivatives (salts, esters, ethers, sugars, nucleotides, nucleosides, peptides and lipids) of these specified active ingredients which are suitable according to the invention.

The amount of the abovementioned antioxidants (one or more compounds) in the emulsions is preferably 0.001 to 30% by weight, particularly preferably 0.05 to 20% by weight, in particular 0.1 to 10% by weight, based on the total weight of the preparation.

If vitamin E and/or derivatives thereof are the antioxidant or the antioxidants, it is advantageous to choose their particular concentrations from the range from 0.001 to 10% by weight, based on the total weight of the formulation.

If vitamin A or vitamin A derivatives, or carotenes or derivatives thereof are the antioxidant or the antioxidants, it is advantageous to choose their particular concentrations from the range from 0.001 to 10% by weight, based on the total weight of the formulation.

Within the scope of the present disclosure, the expression "lipids" is sometimes used as the generic term for fats, oils, waxes and the like, as is entirely familiar to the person skilled in the art. The terms "oil phase" and "lipid phase" are also used synonymously.

Oils and fats differ from one another inter alia in their polarity, which is difficult to define. It has already been proposed to adopt interfacial tension towards water as a measure of the polarity index of an oil or of an oil phase. This means that the greater the polarity of the oil phase in question, the lower the interfacial tension between this oil phase and water. According to the invention, the interfacial tension is regarded as being one possible measure of the polarity of a given oil component.

Polar oils are, for example, those from the group of lecithins and of fatty acid triglycerides, namely the triglycerol esters of saturated and/or unsaturated, branched and/or unbranched alkanecarboxylic acids with a chain length of from 8 to 24, in particular 12 to 18 carbon atoms. The fatty acid triglycerides can, for example, be chosen advantageously from the group of synthetic, semisynthetic and natural oils, such as, for example, olive oil, sunflower oil, soya oil, peanut oil, rapeseed oil, almond oil, palm oil, coconut oil, castor oil, wheatgerm oil, grapeseed oil, thistle oil, evening primrose oil, macadamia nut oil and the like.

Particularly advantageous polar lipids for the purposes of the present invention are all natural lipids such as, for example, olive oil, sunflower oil, soya oil, peanut oil, rapeseed oil, almond oil, palm oil, coconut oil, castor oil, wheatgerm oil, grapeseed oil, thistle oil, evening primrose oil, macadamia nut oil, maize germ oil, avocado oil and the like, and those listed below.

| Trade name | INCI name | Polarity [mN/m] |
| --- | --- | --- |
| Isofol 14 T | Butyl Decanol (+) Hexyl Octanol (+) Hexyl Decanol (+) Butyl Octanol | 19.8 |
| Lipovol MOS-130 | Tridecyl Stearate (+) Tridecyl Trimellitate (+) Dipentaerythrityl Hexacaprylate/Hexacaprate | 19.4 |

| Trade name | INCI name | Polarity [mN/m] |
| --- | --- | --- |
| Castor oil | | 19.2 |
| Isofol Ester 0604 | | 19.1 |
| Miglyol 840 | Propylene Glycol Dicaprylate/Dicaprate | 18.7 |
| Isofol 12 | Butyl Octanol | 17.4 |
| Tegosoft SH | Stearyl Heptanoate | 17.8 |
| Avocado oil | | 14.5 |
| Cetiol B | Dibutyl Adipate | 14.3 |
| Dermol 488 | PEG 2 Diethylene Hexanoate | 10.1 |
| Cosmacol ELI | C12–13 Alkyl Lactate | 8.8 |
| Dermol 489 | Diethylene Glycol Dioctanoate/ Diisononanoate | 8.6 |
| Cosmacol ETI | Di-C12/13 Alkyl Tartrate | 7.1 |
| Emerest 2384 | Propylene Glycol Monoisostearate | 6.2 |
| Myritol 331 | Cocoglycerides | 5.1 |
| Prisorine 2041 GTIS | Triisostearin | 2.4 |

The oil phase can also advantageously be chosen from the group of dialkyl ethers, the group of saturated or unsaturated, branched or unbranched alcohols. It is particularly advantageous if the oil phase has a content of $C_{12-15}$-alkyl benzoate or consists entirely of this.

In addition, the oil phase can advantageously be chosen from the group of Guerbet alcohols. Guerbet alcohols are named after Marcel Guerbet, who described their preparation for the first time. They are formed according to the reaction equation

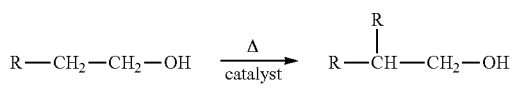

by oxidation of an alcohol to give an aldehyde, by aldol condensation of the aldehyde, elimination of water from the aldol and hydrogenation of the allyl aldehyde. Guerbet alcohols are liquid even at low temperatures and cause virtually no skin irritations. They can be used advantageously as fatting, superfatting and also refatting constituents in skincare and haircare compositions.

The use of Guerbet alcohols in cosmetics is known per se. Such species are then in most cases characterized by the structure

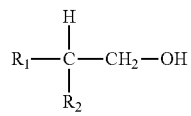

Here, $R_1$ and $R_2$ are usually unbranched alkyl radicals.

According to the invention, the Guerbet alcohol or alcohols are chosen from the group in which
$R_1$=propyl, butyl, pentyl, hexyl, heptyl or octyl and
$R_2$=hexyl, heptyl, octyl, nonyl, decyl, undecyl, dodecyl, tridecyl or tetradecyl.

Guerbet alcohols preferred according to the invention are 2-butyloctanol—it has the chemical structure

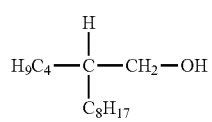

and is available, for example, under the trade name Isofolo® 12 from Condea Chemie GmbH—and 2-hexyldecanol—it has the chemical structure

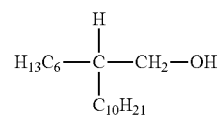

and is available, for example, under the trade name Isofol® 16 from Condea Chemie GmbH. Mixtures of Guerbet alcohols according to the invention are also used advantageously according to the invention. Mixtures of 2-butyloctanol and 2-hexyl-decanol are available, for example, under the trade name Isofol®14 from Condea Chemie GmbH.

The total amount of Guerbet alcohols in the finished cosmetic or dermatological preparations is advantageously chosen from the range up to 25.0% by weight, preferably 0.5-15.0% by weight, based on the total weight of the preparations.

Any desired mixtures of such oil and wax components are also used advantageously for the purposes of the present invention. It may in some cases also be advantageous to use waxes, for example cetyl palmitate, as the sole lipid component of the oil phase.

Particularly advantageous mid-polar lipids for the purposes of the present invention are the substances listed below:

| Trade name | INCI name | Polarity [mN/m] |
| --- | --- | --- |
| DUB VCl 10 | Isodecyl Neopentanoate | 29.9 |
| Dermol IHD | Isohexyl Decanoate | 29.7 |
| Dermol 108 | Isodecyl Octanoate | 29.6 |
| Dihexyl Ether | Dihexyl Ether | 29.2 |
| Dermol 109 | Isodecyl 3,5,5-Trimethyl Hexanoate | 29.1 |
| Cetiol SN | Cetearyl Isononanoate | 28.6 |
| Isopropyl palmitate | Isopropyl Palmitate | 28.8 |
| DC Fluid 345 | Cyclomethicone | 28.5 |
| Dow Corning Fluid 244 | Cyclopolydimethylsiloxan | 28.5 |
| Jojoba oil Gold | | 26.2 |
| Wacker AK 100 | Dimethicone | 26.9 |
| Dermol 98 | 3,5,5-Trimethyl 2-Ethylhexanoate | 26.2 |
| Dow Corning Fluid 246 | Open | 25.3 |
| Eutanol G | Octyldodecanol | 24.8 |
| Isofol 16 | Hexyldecanol | 24.3 |
| Dermol 139 | Isotridecyl 3,5,5-Trimethylhexanonanoate | 24.5 |
| Cetiol PGL | Hexyldecanol (+) Hexyl Decyl Laurate | 24.3 |
| Cegesoft C24 | Octyl Palmitate | 23.1 |
| M.O.D. | Octyldodecyl Myristate | 22.1 |
| Macadamia Nut Oil | | 22.1 |
| Silicone oil VP 1120 | Phenyltrimethicone | 22.7 |
| Isocarb 12 | Butyloctanoic Acid | 22.1 |
| Isopropyl stearate | Isopropyl Stearate | 21.9 |
| Finsolv TN | C12–15 Alkyl Benzoate | 21.8 |
| Dermofeel BGC | Butylene Glycol Caprylate/Caprate | 21.5 |
| Miglyol 812 | Caprylic/Capric Triglyceride | 21.3 |
| Trivent OCG | Tricaprylin | 20.2 |
| Dermol 866 | PEG Diethyl hexanoate/Diisononanoate/ Ethylhexyl Isononanoate | 20.1 |

Nonpolar oils are, for example, those which are chosen from the group of branched and unbranched hydrocarbons and hydrocarbon waxes, in particular Vaseline (petrolatum), paraffin oil, squalane and squalene, polyolefins and hydrogenated polyisobutenes. Among the polyolefins, polydecenes are the preferred substances.

Particularly advantageous nonpolar lipids for the purposes of the present invention are the substances listed below:

| Trade name | INCI name | Polarity [mN/m] |
|---|---|---|
| Ecolane 130 | Cycloparaffin | 49.1 |
| Nexbase 2006 FG | Polydecene | 46.7 |
| Polysynlane | Hydrogenated Polyisobutene | 44.7 |
| Wacker Silicone oil AK 50 | Polydimethylsiloxane | 46.5 |
| Solvent ICH | Isohexadecane | 43.8 |
| Pionier 2076 | Mineral Oil | 43.7 |
| Pionier 6301 | Mineral Oil | 43.7 |
| Wacker Silicone oil AK 35 | Polydimethylsiloxane | 42.4 |
| Isoeicosane | Isoeicosane | 41.9 |
| Wacker Silicone oil AK 20 | Polydimethylsiloxane | 40.9 |
| Isofol 1212 Carbonate | | 40.3 |
| Softcutol O | Ethoxydiglycol Oleate | 40.5 |
| Lipodermanol OL | Decyl Olivate | 40.3 |
| Cetiol S | Dioctylcyclohexane | 39.0 |
| Pionier 2071 | Mineral Oil | 38.3 |
| Hydrobrite 1000 PO | Paraffinum Liquidum | 37.6 |
| Tegosoft HP | Isocetyl Palmitate | 36.2 |
| Isofol Ester 1693 | | 33.5 |
| Isofol Ester 1260 | | 33.0 |
| Dow Corning Fluid 245 | Cyclopentasiloxane | 32.3 |
| Prisorine 2036 | Octyl Isostearate | 31.6 |
| Cetiol CC | Dicaprylyl Carbonate | 31.7 |
| Dermol 99 | Trimethylhexyl Isononanoate | 31.1 |
| Dermol 89 | 2-Ethylhexyl Isononanoate | 31.0 |
| Cetiol OE | Dicaprylyl Ether | 30.9 |
| Dihexyl carbonate | Dihexyl Carbonate | 30.9 |
| Silkflo 366 NF | Polydecene | 30.1 |
| Estol 1540 EHC | Octyl Cocoate | 30.0 |

However, it is also advantageous to use mixtures of lipids with higher and lower polarity and the like. For example the oil phase can advantageously be chosen from the group of branched and unbranched hydrocarbons and hydrocarbon waxes, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids with a chain length of from 8 to 24, in particular 12-18, carbon atoms. The fatty acid triglycerides can, for example, advantageously be chosen from the group of synthetic, semisynthetic and natural oils, e.g. olive oil, sunflower oil, soya oil, peanut oil, rapeseed oil, almond oil, palm oil, coconut oil, palm kernel oil and the like, provided the conditions required in the main claim are observed.

Fat and/or wax components to be used advantageously according to the invention can be chosen from the group of vegetable waxes, animal waxes, mineral waxes and petrochemical waxes. According to the invention, candelilla wax, carnauba wax, Japan wax, esparto grass wax, cork wax, guaruma wax, rice germ oil wax, sugar cane wax, berry wax, ouricury wax, montan wax, jojoba wax, shea butter, beeswax, shellac wax, spermaceti, lanolin (wool wax), uropygial grease, ceresine, ozokerite (earth wax), paraffin waxes and micro waxes, for example, are favourable, provided the conditions required in the main claim are observed.

Further advantageous fat and/or wax components are chemically modified waxes and synthetic waxes, such as, for example those available under the trade names Syncrowax HRC (glyceryl tribehenate), and Syncrowax AW 1C ($C_{18-36}$-fatty acid) from CRODA GmbH, and montan ester waxes, sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkylhydroxystearoyl stearate and/or glycol montanate. In addition, also advantageous are certain organosilicon compounds which have similar physical properties to said fat and/or wax components, such as, for example, stearoxytrimethylsilane, provided the conditions required in the main claim are observed.

According to the invention, the fat and/or wax components can either be present individually or else in a mixture. Any desired mixtures of such oil and wax components are also used advantageously for the purposes of the present invention.

The oil phase is advantageously chosen from the group consisting of 2-ethylhexyl isostearate, octyldodecanol, isotridecyl isononanoate, butylene glycol dicaprylate/dicaprate, 2-ethylhexyl cocoate, $C_{12-15}$-alkyl benzoate, caprylic/capric triglyceride, dicaprylyl ether provided the conditions required in the main claim are observed.

Mixtures of octyldodecanol, caprylic/capric triglyceride, dicaprylyl ether, dicaprylyl carbonate, cocoglycerides, or mixtures of $C_{12-15}$-alkyl benzoate and 2-ethylhexyl isostearate, mixtures of $C_{12-15}$-alkyl benzoate and butylene glycol dicaprylate/dicaprate, and mixtures of $C_{12-15}$-alkyl benzoate, 2-ethylhexyl isostearate and isotridecyl isononanoate are particularly advantageous provided the conditions required in the main claim are observed.

Of the hydrocarbons, paraffin oil, cycloparaffin, squalane, squalene, hydrogenated polyisobutene and/or polydecene are to be used advantageously for the purposes of the present invention, provided the conditions required in the main claim are observed.

It may likewise be advantageous to choose the oil phase of the preparations according to the invention partially or completely from the group of cyclic and/or linear silicones, which are also referred to as "silicone oils" for the purposes of the present disclosure. Such silicones or silicone oils may be in the form of monomers which are generally characterized by structural elements, as follows:

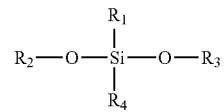

Silicone oils are high molecular weight synthetic polymeric compounds in which silicon atoms are joined via oxygen atoms in a chain-like and/or reticular manner and the remaining valencies of the silicon are saturated by hydrocarbon radicals (in most cases methyl groups, less often ethyl, propyl, phenyl groups, inter alia).

Linear silicones with a plurality of siloxyl units to be used advantageously according to the invention are generally characterized by structural elements as follows:

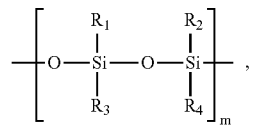

where the silicon atoms may be substituted by identical or different alkyl radicals and/or aryl radicals, which are shown here in general terms by the radicals $R_1$-$R_4$ (that is to say the number of different radicals is not necessarily limited to up to 4). m can here assume values from 2-200,000.

Systematically, the linear silicone oils are referred to as polyorganosiloxanes; the methyl-substituted polyorganosiloxanes, which represent the most important compounds of this group in terms of amount and are characterized by the following structural formula

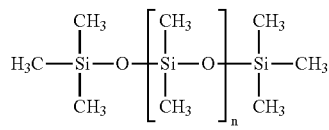

are also referred to as polydimethylsiloxane and Dimethicone (INCI). Dimethicones have various chain lengths and various molecular weights. Dimethicones of various chain lengths and phenyltrimethicones are particularly advantageous linear silicone oils for the purposes of the present invention.

Particularly advantageous polyorganosiloxanes for the purposes of the present invention are also, for example, dimethylpolysiloxanes [poly(dimethylsiloxane)], which are available, for example, under the trade names ABIL 10 to 10 000 from Th. Goldschmidt. Also advantageous are phenylmethylpolysiloxanes (INCI: Phenyl Dimethicone, Phenyl Trimethicone), cyclic silicones (octamethylcyclotetrasiloxane and decamethylcyclopentasiloxane), which are also referred to according to INCI as Cyclomethicone, aminomodified silicones (INCI: Amodimethicone) and silicone waxes, e.g. polysiloxane-polyalkylene copolymers (INCI: Stearyl Dimethicone and Cetyl Dimethicone) and dialkoxydimethylpolysiloxanes (stearoxy dimethicones and behenoxy stearyl dimethicones) which are available as various Abil wax grades from Th. Goldschmidt.

Also particularly advantageous for the purposes of the present invention are the silicone oils listed below:

| Trade name | INCI name | Polarity [mN/m] |
|---|---|---|
| Wacker Silicone oil AK 100 | Polydimethylsiloxane | 26.9 |
| Wacker Silicone oil AK 50 | Polydimethylsiloxane | 46.5 |
| Wacker Silicone oil AK 35 | Polydimethylsiloxane | 42.4 |
| Wacker Silicone oil AK 20 | Polydimethylsiloxane | 40.9 |
| Dow Corning Fluid 245 | Cyclopentasiloxane | 32.3 |
| Dow Corning Fluid 345 | Cyclomethicone | 28.5 |

Cyclic silicones to be used advantageously according to the invention are generally characterized by structural elements as follows

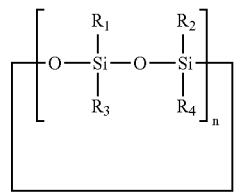

where the silicon atoms may be substituted by identical or different alkyl radicals and/or aryl radicals, which are shown here in general terms by the radicals $R_1$-$R_4$ (that is to say the number of different radicals is not necessarily limited to up to 4). n can here assume values from 3/2 to 20. Fractional values for n take into consideration the fact that uneven numbers of siloxyl groups may be present in the cycle.

Particularly advantageous cyclic silicone oils for the purposes of the present invention are cyclomethicones, in particular cyclomethicone D5 and/or cyclomethicone D6.

Advantageous silicone oils and/or silicone waxes for the purposes of the present invention are cyclic and/or linear silicone oils and silicone waxes.

It is particularly advantageous for the purposes of the present invention to choose the ratio of lipids to silicone oils as approximately 1:1 (generally x:y).

Phenyltrimethicone is advantageously chosen as silicone oil. Other silicone oils, for example dimethicone, phenyldimethicone, cyclomethicone (octamethylcyclotetrasiloxane), for example hexamethylcyclotrisiloxane, polydimethylsiloxane, poly(methylphenylsiloxane), cetyldimethicone, behenoxydimethicone are also to be used advantageously for the purposes of the present invention.

Also advantageous are mixtures of cyclomethicone and isotridecyl isononanoate, and those of cyclomethicone and 2-ethylhexyl isostearate.

It is, however, also advantageous to choose silicone oils of similar constitution to the above-named compounds, whose organic side chains are derivatized, for example polyethoxylated and/or polypropoxylated. These include, for example, polysiloxane-polyalkyl-polyether copolymers, such as cetyldimethicone copolyol and cetyldimethicone copolyol (and) polyglyceryl-4-isostearate (and) hexyl laurate.

The lipid phase can be chosen advantageously from the following group of substances:
    mineral oils, mineral waxes;
    oils, such as triglycerides of capric acid or of caprylic acid, and also natural oils, such as, for example, castor oil;
    fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;
    alkyl benzoates;
    silicone oils, such as dimethylpolysiloxanes, diethylpolysiloxanes, diphenylpolysiloxanes, and mixed forms thereof.

The oil phase of the emulsions, oleogels and hydrodispersions or lipodispersions for the purposes of the present invention is advantageously chosen from the group of esters of saturated and/or unsaturated, branched and/or unbranched alkanecarboxylic acids with a chain length of from 3 to 30 carbon atoms and saturated and/or unsaturated, branched and/or unbranched alcohols with a chain length of from 3 to 30 carbon atoms, from the group of esters of aromatic carboxylic acids and saturated and/or unsaturated, branched and/or unbranched alcohols with a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

Any desired mixtures of such oil and wax components are also used advantageously for the purposes of the present invention. It may in some instances also be advantageous to use waxes, for example cetyl palmitate, as the sole lipid component of the oil phase.

The oil phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric triglyceride, dicaprylyl ether.

Mixtures of $C_{12-15}$-alkyl benzoate and 2-ethylhexyl isostearate, mixtures of $C_{12-15}$-alkyl benzoate and isotridecyl isononanoate, and mixtures of $C_{12-15}$-alkyl benzoate, 2-ethylhexyl isostearate and isotridecyl isononanoate are particularly advantageous.

Of the hydrocarbons, paraffin oil, squalane and squalene are to be used advantageously for the purposes of the present invention.

The aqueous phase of the formulations according to the invention optionally advantageously comprises alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, glycerol, and in particular one or more thickeners which can advantageously be chosen from the group consisting of silicon dioxide, aluminium silicates, polysaccharides and derivatives thereof, e.g. xanthan gum and/or hydroxypropylmethylcellulose, in each case individually or in combination.

It is also advantageous for the purposes of the present invention to create cosmetic and dermatological preparations whose main purpose is not protection against sunlight but which nevertheless contain a content of UV protection substances. Thus, UV-A and/or UV-B filter substances are, for example, usually incorporated into day creams or make-up products. UV protection substances, like antioxidants and—if desired—preservatives, also represent effective protection of the preparations themselves against decay. Also favourable are cosmetic and dermatological preparations which are in the form of a sunscreen composition.

The examples below illustrate the invention. The amounts given are percentages by weight based in each case on the total mass of the preparation. The example preparations according to the invention have a slight green shade and give the skin a natural appearance when applied to irritated or reddened skin. The colour shading of the preparations can be adapted individually within the claimed range depending on the ambient parameters, skin colour, degree of redness.

| W/O emulsions | | | | | |
|---|---|---|---|---|---|
| | Example | | | | |
| | 1 | 2 | 3 | 4 | 5 |
| Triglycerol diisostearate | 1.0 | 0.5 | 0.25 | 2.0 | 3.0 |
| Diglycerol dipolyhydroxystearate | 1.0 | 1.5 | 1.75 | 3.0 | 2.0 |
| Paraffin oil | 12.5 | 10.0 | 8.0 | 5.0 | 17.5 |
| Vaseline | 8.0 | 6.0 | 5.0 | 12.0 | 2.5 |
| Hydrogenated coco glycerides | 2.0 | 1.0 | 2.5 | 5.0 | 0.25 |
| Decyl oleate | 0.5 | 0.75 | 1.0 | 2.0 | 0.25 |
| Octyldodecanol | 0.5 | 1.0 | 0.75 | 3.0 | 0.25 |
| Aluminium stearate | 0.4 | 0.3 | 0.6 | 1.0 | 0.05 |
| Dicaprylyl carbonate | 0.1 | 0.05 | 0.15 | 0.5 | 1.0 |
| Hydrogenated castor oil | 0.5 | 0.75 | 1.0 | 2.5 | 5.0 |
| Magnesium sulphate | 0.5 | 0.6 | 0.5 | 0.7 | 1.0 |
| Glycerol | 3.0 | 5.0 | 10.0 | 15.0 | 1.5 |
| Citric acid | 0.2 | 0.1 | 0.2 | 0.3 | 1.0 |
| Sodium citrate | 0.2 | 0.05 | 0.4 | 0.3 | 2.0 |
| Perfume | q.s. | q.s. | q.s. | q.s. | q.s. |
| Ethanol | 2.0 | — | 5.0 | — | — |
| Caprylic/capric triglyceride | 2.0 | 2.5 | 3.0 | 5.0 | 0.5 |
| Potassium sorbate | 0.04 | 0.15 | 0.05 | 0.03 | 0.4 |
| Benzyl alcohol | 0.3 | 0.4 | 0.25 | 0.15 | — |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | 1.0 | 2.0 | 3.0 | — | — |
| Glycyrrhiza inflata | 0.025 | 0.035 | — | — | 0.25 |
| Hamamelis | 1.0 | 2.0 | — | 5.0 | — |
| Water | ad 100 | ad 100 | ad 100 | ad 100 | ad 100 |

| | Example | | | | |
|---|---|---|---|---|---|
| | 6 | 7 | 8 | 9 | 10 |
| PEG-30 dipolyhydroxystearate | — | 0.5 | 0.25 | — | 3.0 |
| Lanolin alcohol | 1.0 | 1.5 | 1.75 | 3.0 | — |
| Paraffin oil | 12.5 | 10.0 | 8.0 | 5.0 | 17.5 |
| Vaseline | 8.0 | 6.0 | 5.0 | 12.0 | 2.5 |
| Hydrogenated cocoglycerides | 2.0 | 1.0 | 2.5 | 5.0 | 0.25 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Aluminium stearate | 0.4 | 0.3 | 0.6 | 1.0 | 0.05 |
| Dicaprylyl carbonate | 0.1 | 0.05 | 0.15 | 0.5 | 1.0 |
| Hydrogenated castor oil | 0.5 | 0.75 | 1.0 | 2.5 | 5.0 |
| Microcrystalline cellulose | 0.5 | 1.0 | 0.75 | 0.25 | 0.1 |
| Magnesium sulphate | 0.5 | 0.6 | 0.5 | 0.7 | 1.0 |
| Glycerol | 3.0 | 5.0 | 10.0 | 15.0 | 1.5 |
| Citric acid | 0.2 | 0.1 | 0.2 | 0.3 | 1.0 |
| Perfume | q.s. | q.s. | q.s. | q.s. | q.s. |
| 1,3-Butylene glycol | 2.0 | — | 5.0 | — | — |
| Caprylic/capric triglyceride | 2.0 | 2.5 | 3.0 | 5.0 | 0.5 |
| Sodium dehydracetate | — | — | 0.05 | — | — |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | 1.0 | 2.0 | 3.0 | — | — |
| Glycyrrhiza inflata | 0.025 | 0.035 | — | — | 0.25 |
| Hamamelis | 1.0 | 2.0 | — | 5.0 | — |
| Potassium sorbate | 0.3 | 0.4 | 0.25 | 0.15 | — |
| Water | ad 100 | ad 100 | ad 100 | ad 100 | ad 100 |

W/S Emulsion

| | Example | | | | |
|---|---|---|---|---|---|
| | 11 | 12 | 13 | 14 | 15 |
| Cetyl PEG/PPG-10/1 dimethicones | 1.0 | — | — | 3.0 | 5.0 |
| Cyclomethicone + PEG/PPG-18/18 dimethicone (90:10) | 10.0 | 12.5 | 25 | — | — |
| Cyclomethicone | 12.5 | 15 | 28.0 | 25.0 | 17.5 |
| Dimethicone | 5.0 | 13.0 | 5.0 | 12.0 | 15.0 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Sodium chloride | 2.0 | 0.6 | 2.5 | 0.7 | 1.0 |
| Glycerol | 3.0 | 5.0 | 10.0 | 15.0 | 1.5 |
| Citric acid | 0.2 | 0.1 | 0.2 | 0.3 | 1.0 |
| Sodium citrate | 1.0 | 0.1 | 0.4 | 0.9 | 2.5 |
| Perfume | q.s. | q.s. | q.s. | q.s. | q.s. |
| Potassium sorbate | 0.4 | 0.1 | 0.05 | 0.3 | 0.4 |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | 1.0 | 2.0 | 3.0 | — | — |
| Glycyrrhiza inflata | 0.025 | 0.035 | — | — | 0.25 |
| Hamamelis | 1.0 | 2.0 | — | 5.0 | — |
| Cetyldimethicone | 0.5 | — | 0.7 | — | — |
| Benzyl alcohol | — | — | 0.05 | — | 0.1 |
| Water | ad 100 | ad 100 | ad 100 | ad 100 | ad 100 |

| | Example | | | | |
|---|---|---|---|---|---|
| | 16 | 17 | 18 | 19 | 20 |
| Cetyl PEG/PPG-10/1 dimethicones | 1.0 | — | — | 3.0 | 5.0 |
| Cyclomethicone + PEG/PPG-18/18 dimethicone (90:10) | 10.0 | 12.5 | 25 | — | — |
| Cyclomethicone | 12.5 | 15 | 28.0 | 25.0 | 17.5 |
| Dimethicone | 5.0 | 13.0 | 5.0 | 12.0 | 15.0 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Sodium chloride | 2.0 | 0.6 | 2.5 | 0.7 | 1.0 |
| Glycerol | 3.0 | 5.0 | 10.0 | 15.0 | 1.5 |
| Lactic acid | 0.2 | 0.1 | 0.2 | — | — |
| Sodium lactate | 0.2 | 1.0 | 0.05 | — | — |
| Perfume | q.s. | q.s. | q.s. | q.s. | q.s. |
| Stearyldimethicone | 0.5 | — | 0.7 | — | — |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | 1.0 | 2.0 | 3.0 | — | — |
| Glycyrrhiza inflata | 0.025 | 0.035 | — | — | 0.25 |
| Hamamelis | 1.0 | 2.0 | — | 5.0 | — |
| Dehydracetic acid | — | — | 0.05 | — | 0.1 |
| Modified starch | — | 2.5 | — | 0.15 | — |
| Water | ad 100 | ad 100 | ad 100 | ad 100 | ad 100 |

W/O emulsions

| | Example | | | | |
|---|---|---|---|---|---|
| | 21 | 22 | 23 | 24 | 25 |
| TPEG-22 dodecyl glycol copolymer | 5.0 | 1.5 | 0.25 | — | 3.0 |
| PEG-45 dodecyl glycol polymer | 1.0 | 1.5 | 1.75 | 3.0 | — |
| Paraffin oil | 12.5 | 10.0 | 8.0 | 5.0 | 17.5 |
| Isopropyl stearate | 8.0 | 6.0 | 5.0 | 12.0 | 2.5 |
| Hydrogenated cocoglycerides | 2.0 | 1.0 | 2.5 | 5.0 | 0.25 |
| Evening primrose oil | 0.5 | 0.75 | 1.0 | 2.0 | 0.25 |
| Octyldodecanol | 0.5 | 1.0 | 0.75 | 3.0 | 0.25 |
| Aluminium stearate | 0.4 | 0.3 | 0.6 | 1.0 | 0.05 |
| Dicaprylyl carbonate | 0.1 | 0.05 | 0.15 | 0.5 | 1.0 |
| Hydrogenated castor oil | 0.5 | 0.75 | 1.0 | 2.5 | 5.0 |
| Magnesium sulphate | 0.5 | 0.6 | 0.5 | 0.7 | 1.0 |
| Glycerol | 3.0 | 5.0 | 10.0 | 15.0 | 1.5 |
| Sodium citrate | 0.2 | 0.1 | — | — | — |
| Citric acid | 0.2 | 0.1 | — | — | — |
| Perfume | q.s. | q.s. | q.s. | q.s. | q.s. |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | 1.0 | 2.0 | 3.0 | — | — |
| Glycyrrhiza inflata | 0.025 | 0.035 | — | — | 0.25 |
| Hamamelis | 1.0 | 2.0 | — | 5.0 | — |
| 1,3-Butylene glycol | 2.0 | — | 5.0 | — | — |
| Caprylic/capric triglyceride | 2.0 | 2.5 | 3.0 | 5.0 | 0.5 |
| Potassium sorbate | 0.4 | 0.15 | 0.05 | 0.3 | 0.4 |
| Benzyl alcohol | — | — | 0.05 | — | 0.1 |
| Water | ad 100 | ad 100 | ad 100 | ad 100 | ad 100 |

| | Example | | | | |
|---|---|---|---|---|---|
| | 26 | 27 | 28 | 29 | 30 |
| Polyglyceryl-2-dipolyhydroxystearate | 3.0 | — | 0.25 | — | 3.0 |
| Polyglyceryl-3-diisostearate | 1.0 | 3.5 | 1.75 | 2.5 | — |
| PEG-40 sorbitan isostearate | — | 2.5 | 0.5 | 3.5 | 3.0 |
| Paraffin oil | 12.5 | 10.0 | 8.0 | 5.0 | 17.5 |
| Isopropyl stearate | 8.0 | 6.0 | 5.0 | 12.0 | 2.5 |
| Hydrogenated cocoglycerides | 2.0 | 1.0 | 2.5 | 5.0 | 0.25 |
| Isopropyl palmitate | 0.5 | 1.0 | 0.75 | 3.0 | 0.25 |
| Dicaprylyl carbonate | 0.1 | 0.05 | 0.15 | 0.5 | 1.0 |
| Hydrogenated castor oil | 0.5 | 0.75 | 1.0 | 2.5 | 5.0 |
| Magnesium sulphate | 0.5 | 0.6 | 0.5 | 0.7 | 1.0 |
| Glycerol | 3.0 | 5.0 | 10.0 | 15.0 | 1.5 |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | 1.0 | 2.0 | 3.0 | — | — |
| Glycyrrhiza inflata | 0.025 | 0.035 | — | — | 0.25 |
| Hamamelis | 1.0 | 2.0 | — | 5.0 | — |
| Citric acid | 0.2 | 0.1 | 0.1 | 0.3 | 1.0 |
| Sodium citrate | 0.2 | 0.3 | 0.2 | 1.5 | 0.8 |
| Perfume | q.s. | q.s. | q.s. | q.s. | q.s. |
| Caprylic/capric triglyceride | 2.0 | 2.5 | 3.0 | 5.0 | 0.5 |
| Potassium sorbate | 0.24 | 0.15 | 0.05 | 0.3 | 0.4 |
| Water | ad 100 | ad 100 | ad 100 | ad 100 | ad 100 |

Silicone-in-water emulsion

| | Example | | | | |
|---|---|---|---|---|---|
| | 31 | 32 | 33 | 34 | 35 |
| Dimethicone copolyol, caprylic/capric triglyceride | 1.0 | 2.0 | 8.0 | 3.0 | 5.0 |
| Cyclomethicone | 12.5 | 15 | 25.0 | 10.0 | 7.5 |
| Dimethicone | 5.0 | 15.0 | 5.0 | 12.0 | 15.0 |
| Mineral oil | 0.5 | 0.75 | 1.0 | 2.0 | 0.25 |
| Phenyltrimethicone | 0.5 | 1.0 | 0.75 | 3.0 | 0.25 |
| Glycerol | 5.0 | 7.5 | 10.0 | 3.0 | 1.0 |
| Xanthan gum | — | 0.1 | — | 0.25 | 1.0 |
| Perfume | q.s. | q.s. | q.s. | q.s. | q.s. |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | 1.0 | 2.0 | 3.0 | — | — |
| Glycyrrhiza inflata | 0.025 | 0.035 | — | — | 0.25 |
| Hamamelis | 1.0 | 2.0 | — | 5.0 | — |
| Methylparaben | 0.4 | 0.1 | 0.05 | 0.3 | 0.4 |
| Propylparaben | 0.3 | 0.4 | 0.25 | 0.15 | — |
| Iodopropynyl butylcarbamate | — | — | 0.05 | — | 0.1 |
| Water | ad 100 | ad 100 | ad 100 | ad 100 | ad 100 |

O/W emulsion

| | Example | | | | |
|---|---|---|---|---|---|
| | 36 | 37 | 38 | 39 | 40 |
| Glyceryl stearate | 1.0 | — | — | 0.5 | 0.25 |
| Polyethylene glycol(40) stearate | 10.0 | — | 5 | — | — |
| Triglycerol methylglucose distearate | — | 5.5 | — | — | 2.5 |
| Sorbitan stearate | — | 1.5 | 3 | — | — |
| Cyclomethicone | 2.5 | 15 | 8.0 | 5.0 | 7.5 |
| Dimethicone | 5.0 | 3.0 | 5.0 | 2.0 | 5.0 |
| Behenyl alcohol | 1 | — | 2 | 1 | — |
| Stearyl alcohol | — | 1 | — | 1 | — |
| Cetylstearyl alcohol | — | — | 1 | 1 | — |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Perfume | q.s. | q.s. | q.s. | q.s. | q.s. |
| Methylparaben | 0.4 | 0.1 | 0.05 | 0.3 | 0.4 |
| Propylparaben | 0.3 | 0.4 | 0.25 | 0.15 | — |
| Iodopropynyl butylcarbamate | — | — | 0.05 | — | 0.1 |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | 1.0 | 2.0 | 3.0 | — | — |
| Glycyrrhiza inflata | 0.025 | 0.035 | — | — | 0.25 |
| Hamamelis | 1.0 | 2.0 | — | 5.0 | — |
| Glycerol | 5 | 10 | 3 | 15 | 7.5 |
| Modified starch | — | 2.5 | — | 0.15 | — |
| Water | ad 100 | ad 100 | ad 100 | ad 100 | ad 100 |

O/W emulsion

| | Example | | | | |
|---|---|---|---|---|---|
| | 41 | 42 | 43 | 44 | 45 |
| Polyethylene glycol(21) stearyl ether | 1 | — | 2.5 | 2 | 1.5 |
| Polyethylene glycol(2) stearyl ether | 1 | — | 5.5 | 3 | 7.5 |
| Cetearyl glucoside | — | 8 | — | — | — |
| Behenyl alcohol | 3 | 2 | — | 1 | — |
| Stearyl alcohol | 3 | 2 | — | 2 | — |
| Cetylstearyl alcohol | 3 | 4 | — | — | 2 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Glycerol | 5 | 10 | 15 | 3 | 7.5 |
| Perfume | q.s. | q.s. | q.s. | q.s. | q.s. |
| Methylparaben | 0.4 | 0.1 | 0.05 | 0.3 | 0.4 |
| Propylparaben | 0.3 | 0.4 | 0.25 | 0.15 | — |
| Iodopropynyl butylcarbamate | — | — | 0.05 | — | 0.1 |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | 1.0 | 2.0 | 3.0 | — | — |
| Glycyrrhiza inflata | 0.025 | 0.035 | — | — | 0.25 |
| Hamamelis | 1.0 | 2.0 | — | 5.0 | — |
| Modified starch | 0.5 | — | — | 0.15 | — |
| Water | ad 100 | ad 100 | ad 100 | ad 100 | ad 100 |

| | Example | | | | |
|---|---|---|---|---|---|
| | 46 | 47 | 48 | 49 | 50 |
| Glyceryl stearate citrate | 1.0 | 0.5 | 0.1 | 0.5 | 0.3 |
| Polyethylene glycol(20) cetearyl ether | 10.0 | 1.0 | 5 | — | — |
| Triglycerol methylglucose distearate | — | — | — | — | 2.5 |
| Dimethicone | 0.5 | 3.0 | 0.75 | 1.5 | 0.2 |
| Dicaprylyl carbonate | 3 | 5 | 10 | 15 | 5 |
| Stearyl alcohol | — | — | — | 1 | 0.2 |
| Cetylstearyl alcohol | — | — | 1 | 1 | 0.2 |
| Tocopherol | 0.5 | 0.5 | 0.75 | 0.25 | 0.1 |
| Octyldodecanol | 0.5 | — | 0.75 | 3.0 | 0.25 |
| Carbomer | 0.05 | 0.35 | 0.15 | 0.1 | — |
| Perfume | q.s. | q.s. | q.s. | q.s. | q.s. |
| Caprylic/capric triglyceride | 1 | 5 | 3 | 5 | 10 |
| Methylparaben | 0.4 | 0.3 | 0.05 | 0.3 | 0.4 |
| Iodopropynyl butylcarbamate | — | — | 0.05 | — | 0.1 |
| Phenoxyethanol | — | 0.5 | — | 0.15 | — |
| Sorbitol | 10 | — | — | 5 | — |
| Butylene glycol | — | — | — | 5 | 10 |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | 1.0 | 2.0 | 3.0 | — | — |
| Glycyrrhiza inflata | 0.025 | 0.035 | — | — | 0.25 |
| Hamamelis | 1.0 | 2.0 | — | 5.0 | — |
| Propylene glycol | — | — | 10 | 5 | — |
| Glycerol | — | 7.5 | — | — | — |
| Water | ad 100 | ad 100 | ad 100 | ad 100 | ad 100 |

| | Example | | | | |
|---|---|---|---|---|---|
| | 51 | 52 | 53 | 54 | 55 |
| Sorbitan stearate | 0.86 | — | — | 2.7 | 2.6 |
| Titanium dioxide | 1.5 | 4.0 | 3.75 | 3.1 | 5.5 |
| Shea butter | 1.5 | 2.5 | 3.75 | — | 3.0 |

-continued

| O/W emulsion | | | | | |
|---|---|---|---|---|---|
| Triglycerol methylglucose distearate | 2.14 | 3.0 | 3.0 | 0.6 | 1.2 |
| Squalane | 2.0 | — | — | 4.0 | 3.5 |
| Dimethicone | 4.0 | 3.0 | 5.0 | 3.0 | 2.75 |
| Lauroyllysine | 2.0 | 3.0 | 1.5 | 1.25 | — |
| Ethylhexyl methoxycinnamate | 7.5 | — | — | 1.3 | 1.3 |
| C12-15 alkyl benzoate | 2.0 | 2.5 | 3.75 | 3.0 | 4.5 |
| Phenoxyethanol | 0.5 | 0.4 | 0.4 | 0.75 | 0.5 |
| Methylparaben | 0.3 | 0.2 | 0.2 | 0.2 | 0.2 |
| Glycerol | 10.0 | 10.0 | 10.0 | 10.0 | 12.5 |
| Propylparaben | 0.1 | 0.1 | 0.1 | 0.1 | 0.1 |
| Xanthan gum | 0.2 | 0.1 | 0.1 | 0.2 | 0.1 |
| White pigment (CI 77891) | 2.5 | 3.0 | 2.25 | 3.5 | 5.0 |
| Green pigment (CI 77288) | 0.27 | 0.42 | 0.54 | 0.35 | 0.75 |
| Green pigment (CI 77288) | 0.088 | 0.1 | 0.16 | 0.095 | 0.25 |
| Blue pigment (CI 77007) | 0.03 | 0.04 | 0.05 | 0.03 | 0.08 |
| Panthenol | — | 2.0 | 3.0 | — | — |
| Glycyrrhiza inflata | 0.025 | 0.035 | — | — | 0.25 |
| Hamamelis | — | 2.0 | — | 5.0 | — |
| Perfume | q.s. | q.s. | q.s. | q.s. | q.s. |
| Magnesium aluminium silicate | 0.3 | — | — | — | 0.5 |
| Butylene glycol | 0.5 | 0.018 | 0.018 | — | 0.018 |
| Water | ad 100 | ad 100 | ad 100 | ad 100 | ad 100 |

| Emulsions for concealer application | | | | | |
|---|---|---|---|---|---|
| | Example | | | | |
| | 56 | 57 | 58 | 59 | 60 |
| Triglycerol diisostearate | 5.12 | 4.25 | 3.75 | 6.22 | 5.26 |
| Cyclopentasiloxane | 14.8 | 10.8 | 8.5 | 16.7 | 12.3 |
| Propylene glycol dicaprylate/dicaprate | 6.23 | 10.0 | 8.0 | 5.0 | 5.96 |
| Methyl methacrylate crosspolymer | 4.15 | 3.18 | 5.0 | 4.35 | 2.5 |
| Glyceryl oleate | 2.5 | 1.5 | 2.5 | 3.5 | 2.75 |
| Vaseline | 2.23 | 3.23 | 1.23 | 1.95 | 2.45 |
| Candelilla wax | 1.11 | 1.0 | 0.75 | 2.2 | 0.25 |
| Carnauba wax | 1.11 | 0.3 | 0.6 | 1.0 | 0.25 |
| Acrylate/octylacrylamide copolymer | 1.0 | 1.5 | 0.75 | 1.25 | 1.0 |
| Dimethicone crosspolymer | 0.67 | 0.75 | 1.0 | 0.5 | 0.88 |
| Panthenol | 0.5 | 0.6 | 0.5 | 0.7 | 1.0 |
| Glycerol | 8.5 | 5.0 | 10.0 | 15.0 | 1.5 |
| Butylene glycol | 0.3 | 0.1 | 0.2 | 0.3 | 1.0 |
| EDTA, disodium salt | 0.2 | 0.05 | 0.4 | 0.3 | 0.18 |
| Perfume | — | q.s. | — | q.s. | — |
| PEG/PPG-18/18 dimethicone | 0.11 | 0.05 | 0.25 | 0.12 | 0.13 |
| White pigment (CI 77891) | 8.0 | 10.0 | 6.0 | 8.3 | 5.0 |
| Green pigment (CI 77288) | 0.81 | 0.42 | 0.54 | 0.35 | 0.75 |
| Iron oxide (CI 77492) | 0.152 | 0.1 | 0.16 | 0.095 | 0.25 |
| Mica | 1.67 | 1.87 | 1.47 | 1.65 | — |
| Glycyrrhiza inflata | 0.025 | 0.035 | 0.025 | 0.01 | 0.25 |
| Diazolidinylurea | 0.2 | 0.2 | 0.2 | 0.18 | 0.2 |
| Iodopropynyl butylcarbamate | 0.016 | 0.018 | 0.016 | 0.018 | 0.018 |
| Phenoxyethanol | 0.15 | 0.25 | 0.15 | 0.2 | 0.3 |
| Hamamelis | — | 2.0 | — | 5.0 | — |
| Water | ad 100 | ad 100 | ad 100 | ad 100 | ad 100 |

That which is claimed:

1. A cosmetic or dermatological preparation, wherein the preparation comprises from 0.01% to 5% by weight of at least one red light-filtering dye, at least one white pigment, and from 0.0001% to 10% by weight of at least one anti-inflammatory active ingredient which comprises at least one aqueous extract of *Glycyrrhiza inflate*, and wherein the preparation does not contain strontium cations.

2. The preparation of claim 1, wherein the at least one anti-inflammatory active ingredient further comprises *Hamamelis*.

3. The preparation of claim 1, wherein the at least one anti-inflammatory active ingredient further comprises panthenol.

4. The preparation of claim 2, wherein the at least one anti-inflammatory active ingredient further comprises panthenol.

5. The preparation of claim 1, wherein the at least one anti-inflammatory active ingredient further comprises chamomile extract.

6. The preparation of claim 1, wherein the at least one aqueous extract is present in a concentration of from 0.01% to 2% by weight.

7. The preparation of claim 4, wherein the preparation comprises from 0.01% to 2% by weight of the at least one aqueous extract of *Glycyrrhiza inflata*, at least 1% by weight of *Hamamelis* and at least 1% by weight of panthenol.

8. The preparation of claim 1, wherein the red light-filtering dye comprises at least one green pigment.

9. The preparation of claim 8, wherein the at least one green pigment comprises at least one of Colorona Brilliant Green, Colorona Egyptian Emerald, Timiron Splendid Green, Vert Oxyde Crome Anhydre N, Vert Oxyde Crome Hydrate W886 and Outremer Supercosmetique W 6803.

10. The preparation of claim 8, wherein the at least one green pigment comprises at least one of CI 77288 and CI 77289.

11. The preparation of claim 8, wherein the at least one green pigment is present in a concentration of from 0.08% to 0.25% by weight.

12. The preparation of claim 1, wherein the preparation comprises at least 2.25% by weight of the at least one white pigment.

13. The preparation of claim 12, wherein the at least one white pigment comprises at least one of titanium dioxide, bismuth oxide, and barium sulfate.

14. The preparation of claim 12, wherein the at least one white pigment comprises CI 77891.

15. The preparation of claim 1, wherein the preparation further comprises at least one blue pigment.

16. The preparation of claim 15, wherein a weight ratio of the at least one blue pigment to the at least one red light-filtering dye is from 1:1 to 1:100.

17. The preparation of claim 15, wherein the at least one blue pigment comprises CI 77007.

18. The preparation of claim 1, wherein the preparation further comprises PPG-6 decyltetradeceth-30.

19. The preparation of claim 18, wherein the preparation further comprises butylene glycol.

20. The preparation of claim 1, wherein the preparation is present in the form of an emulsion.

21. The preparation of claim 20, wherein the emulsion is a W/O emulsion or an O/W emulsion.

22. The preparation of claim 20, wherein the emulsion is a W/S emulsion or a S/W emulsion.

23. A cosmetic or dermatological preparation, wherein the preparation comprises from 0.01% to 0.25% by weight of at least one green pigment, at least 2.25% by weight of at least one white pigment, at least one blue pigment, a weight ratio of the at least one blue pigment to the at least one green pigment being from 1:1 to 1:100, and from 0.0001% to 10% by weight of at least one anti-inflammatory active ingredient which comprises at least on aqueous extract of *Glycyrrhiza inflata*, and wherein the preparation does not contain strontium cations.

24. The preparation of claim 23, wherein the preparation comprises at least 0.1% by weight of the at least one green pigment.

25. The preparation of claim 23, wherein the at least one anti-inflammatory active ingredient further comprises at least one of *Hamamelis* and panthenol.

26. The preparation of claim 25, wherein the preparation comprises from 0.01% to 5% by weight of at least one aqueous extract of *Glycyrrhiza inflata*, at least 1% by weight of *Hamamelis* and at least 1% by weight of panthenol.

27. The preparation of claim 23, wherein the at least one green pigment comprises at least one of Colorona Brilliant Green, Colorona Egyptian Emerald, Timiron Splendid Green, Vert Oxyde Crome Anhydre N, Vert Oxyde Crome Hydrate W886 and Outremer Supercosmetique W 6803.

28. The preparation of claim 23, wherein the at least one green pigment comprises at least one of CI 77288 and CI 77289.

29. The preparation of claim 28, wherein the at least one blue pigment comprises CI 77007.

30. The preparation of claim 29, wherein the at least one white pigment comprises CI 77891.

31. The preparation of claim 23, wherein the at least one green pigment comprises at least one of CI 77491, CI 77499 and CI 77492.

32. The preparation of claim 23, wherein the preparation further comprises PPG-6 decyltetradeceth-30.

33. A cosmetic or dermatological preparation, wherein the preparation comprises from 0.1% to 0.2% by weight of at least one green pigment selected from CI 77288 and CI 77289, at least one blue pigment in a weight ratio of the at least one blue pigment to the at least one green pigment of from 1:1 to 1:100, and from 0.0001% to 10% by weight of at least one anti-inflammatory active ingredient which comprises at least one aqueous extract of *Glycyrrhiza inflata*, and wherein the preparation does not contain strontium cations.

34. The preparation of claim 33, wherein the preparation is present in the form of an emulsion.

35. The preparation of claim 33, wherein the preparation further comprises PPG-6 decyltetradeceth-30.

36. The preparation of claim 33, wherein the at least one blue pigment comprises CI 77007.

37. The preparation of claim 33, wherein the preparation further comprises at least one white pigment.

38. The preparation of claim 37, wherein the at least one white pigment comprises at least one of bismuth oxide and barium sulfate.

* * * * *